(12) United States Patent
Ramaswami et al.

(10) Patent No.: US 10,929,413 B2
(45) Date of Patent: Feb. 23, 2021

(54) SUGGESTION-BASED DIFFERENTIAL DIAGNOSTICS

(71) Applicant: Google LLC, Mountain View, CA (US)

(72) Inventors: Prem Ramaswami, Mountain View, CA (US); Frederico Quintao, Belo Horizonte (BR); Kapil Parakh, Washington, DC (US)

(73) Assignee: Google LLC, Mountain View, CA (US)

( * ) Notice: Subject to any disclaimer, the term of this patent is extended or adjusted under 35 U.S.C. 154(b) by 569 days.

(21) Appl. No.: 14/940,304

(22) Filed: Nov. 13, 2015

(65) Prior Publication Data

US 2017/0140008 A1    May 18, 2017

(51) Int. Cl.
  *G06F 16/248*       (2019.01)
  *G06F 16/2457*      (2019.01)
  *G16H 50/20*        (2018.01)

(52) U.S. Cl.
  CPC ...... *G06F 16/248* (2019.01); *G06F 16/24575* (2019.01); *G16H 50/20* (2018.01)

(58) Field of Classification Search
  CPC ......... G06F 17/30554; G06F 17/30528; G06F 19/345
  USPC ....................................................... 770/722
  See application file for complete search history.

(56) References Cited

U.S. PATENT DOCUMENTS

| | | | |
|---|---|---|---|
| 8,473,489 B1 | 6/2013 | Lasko et al. | |
| 8,607,138 B2* | 12/2013 | Harold | G06F 17/30592 707/609 |
| 2007/0061301 A1* | 3/2007 | Ramer | G06F 17/30867 |
| 2011/0004628 A1* | 1/2011 | Armstrong | G06F 17/30672 707/778 |
| 2012/0185498 A1* | 7/2012 | Loofbourrow | G06F 16/90324 707/767 |
| 2013/0036121 A1* | 2/2013 | Kim | G06F 16/954 707/740 |
| 2015/0269176 A1 | 9/2015 | Marantz et al. | |
| 2016/0048651 A1* | 2/2016 | Papier | G06F 19/324 382/128 |
| 2016/0098394 A1* | 4/2016 | Bruno | G06F 17/271 704/9 |
| 2016/0117470 A1* | 4/2016 | Welsh | G06F 16/9535 705/3 |

(Continued)

OTHER PUBLICATIONS

Aschwanden, "Google Flunks Out of Medical School," Popular Science, Jun. 2015, 1 page.

(Continued)

*Primary Examiner* — Alford W Kindred
*Assistant Examiner* — Soheila (Gina) Davanlou
(74) *Attorney, Agent, or Firm* — Fish & Richardson P.C.

(57) ABSTRACT

Methods, including computer programs encoded on a computer storage medium, for indexing native application data. In one aspect, a method includes: receiving a partial search query, determining that the partial search query is classified as a symptom query, in response to determining that the partial search query is classified as a symptom query, identifying one or more differential diagnosis terms, generating a suggested search query based at least on (i) the partial search query, and (ii) one or more of the differential diagnosis terms, and providing the suggested search query in response to the partial search query.

14 Claims, 4 Drawing Sheets

(56) References Cited

U.S. PATENT DOCUMENTS

2016/0224732 A1* 8/2016 Xing .................... G06F 19/322

OTHER PUBLICATIONS

Sevenster et al. " SNOMED CT Saves Keystrokes: Quantifying Semantic Autocompleteion," AMIA, Annual Symposium Proceedings, Nov. 13, 2010, 5 pages.

Sevenster et al. "Algorithmic and user study of an autocompleteion algorithm on a large medical vocabulary," Journal of Biomedical Informatics, vol. 45, No. 1, Feb. 1, 2012, 13 pages.

Hyvonen et al. "Semantic autocompletion," The Semantic Web—ASWC 2006: First Asian Semantic Web Conference, Beijing China, Sep. 3-7, 2006, 13 pages.

International Search Report and Written Opinion in International Application No. PCT/US2016/056334, dated Jan. 25, 2017, 17 pages.

International Preliminary Report on Patentability issued in International Application No. PCT/US2016/056334, dated May 24, 2018, 11 pages.

EP Office Action in European Application No. 16791476, dated Mar. 13, 2020, 7 pages.

* cited by examiner

SUGGESTION-BASED DIFFERENTIAL DIAGNOSTICS

FIELD

The present specification relates to search engines.

BACKGROUND

As the amount of health-related information available on the Internet has dramatically increased, users have a difficult time formulating effective search queries for information pertinent to their specific health issues. This is in part because health has a unique terminology and the formulation of queries in lay terms result in lexicon mismatch. Although mechanisms such as search query suggestions are sometimes provided to help users formulate search queries, they may be ineffective for handling queries for health-related information. As a result, health-related search results have become a source of unfounded concern about common symptomatology for many users.

SUMMARY

In a medical encounter, health professionals map a patient's presentation of one or more symptoms to a list of possible diagnoses called a "differential diagnosis." During the course of the encounter, health professionals may ask clarifying questions to make sure this list of possible diagnoses is complete and ordered from most likely to least likely. Health professionals may utilize each of the patient's answers to rule out a set of conditions as well as guide the next question, thereby narrowing the list down to the most probabilistic diagnoses.

The techniques described herein may allow users to more easily formulate effective health-related search queries by providing search queries suggestions to each user using a methodology similar to that deployed when generating a differential diagnosis. That is, the search engine may operate to identify medical conditions that may be associated with one or more terms included in a user's search query and provide the user with suggested search queries that may lead the user to results with information pertinent to their specific health issues.

In taking a differential diagnosis approach, the search engine may operate with the objective of ruling out medical conditions that may not be pertinent to the specific health issues at hand in order to efficiently arrive at suggested search queries directed to more likely diagnoses. However, instead of outright asking each user a series of questions, as a health care professional generating a differential diagnosis might do to narrow down the list of possible diagnoses, the techniques described herein allow for inferences to be made on the relevancy of different medical conditions by providing each user with suggested search queries or query completions in a strategic manner and evaluating each user's interaction with the suggested search queries provided.

As each user enters their search query, a search engine implementing the techniques described herein may provide each user with suggested search queries that are directed to medical symptoms, risk factors, or other pertinent facts, which may serve to guide each user in formulating a search query that will yield pertinent search results. Furthermore, the search engine may make inferences about the relevancy of one or more medical conditions based on the user's response to being presented with suggested search queries that are directed to symptoms associated with the one or more medical conditions. In this way, the search engine may be able to refine its list of possible diagnoses as a user enters their search query and update search query suggestions in real-time to exclude suggestions directed to irrelevant medical conditions and hone in on the health-related information that matters to the user.

For situations in which the systems discussed here collect personal information about users, or may make use of personal information, the users may be provided with an opportunity to control whether programs or features collect personal information, e.g., information about a user's social network, social actions or activities, profession, a user's preferences, or a user's current location, or to control whether and/or how to receive content from the viewed content server that may be more relevant to the user. In addition, certain data may be anonymized in one or more ways before it is stored or used, so that personally identifiable information is removed. For example, a user's identity may be anonymized so that no personally identifiable information can be determined for the user, or a user's geographic location may be generalized where location information is obtained, such as to a city, zip code, or state level, so that a particular location of a user cannot be determined. Thus, the user may have control over how information is collected about him or her and used by a content server.

In some aspects, the subject matter described in this specification may be embodied in methods that may include the actions of receiving a partial search query, determining that the partial search query is classified as a symptom query, in response to determining that the partial search query is classified as a symptom query, identifying one or more differential diagnosis terms, generating a suggested search query based at least on (i) the partial search query, and (ii) one or more of the differential diagnosis terms, and providing the suggested search query in response to the partial search query.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

In some implementations, the actions may include identifying a medical condition associated with the partial search query in response to determining that the partial search query is classified as a symptom query, where identifying one or more differential diagnosis terms includes identifying one or more terms that are associated with a symptom of the medical condition.

In some examples, actions may include accessing a handcrafted differential diagnosis database for the medical condition associated with the partial search query, where identifying one or more terms that are associated with a symptom of the medical condition includes identifying one or more terms that are associated with a symptom of the medical condition based on the handcrafted differential diagnosis database for the medical condition associated with the partial search query. In one aspect, determining that the partial search query is classified as a symptom query may include classifying the partial search query against multiple symptom query classifiers that are each associated with different medical conditions.

In some implementations, generating the suggested search query based at least on (i) the partial search query, and (ii) one or more of the differential diagnosis terms may include generating a suggested search query based at least on (i) the partial search query, (ii) one or more of the differential diagnosis terms, and (iii) one or more complete terms that are associated with the partial search query. In some examples, generating the suggested search query based at least on (i) the partial search query, and (ii) one or more of the differential diagnosis terms may include generating a suggested search query based at least on (i) the partial search query, (ii) one or more of the differential diagnosis terms, and (iii) one or more previously-suggested search queries that were not selected.

In one aspect, identifying one or more differential diagnosis terms may include identifying one or more differential diagnosis terms based on one or more recent popular queries. In some instances, identifying one or more differential diagnosis terms may include identifying one or more differential diagnosis terms based on a statistical model. In some implementations, determining that the partial search query is classified as a symptom query may include determining that the partial search query is classified as a search query that includes at least a portion of a term corresponding to a symptom of one or more medical conditions.

The details of one or more implementations are set forth in the accompanying drawings and the description below. Other potential features and advantages will become apparent from the description, the drawings, and the claims.

Other implementations of these aspects include corresponding systems, apparatus and computer programs, configured to perform the actions of the methods, encoded on computer storage devices.

BRIEF DESCRIPTION OF THE DRAWINGS

Like reference symbols in the various drawings indicate like elements.

DETAILED DESCRIPTION

Figure 1:
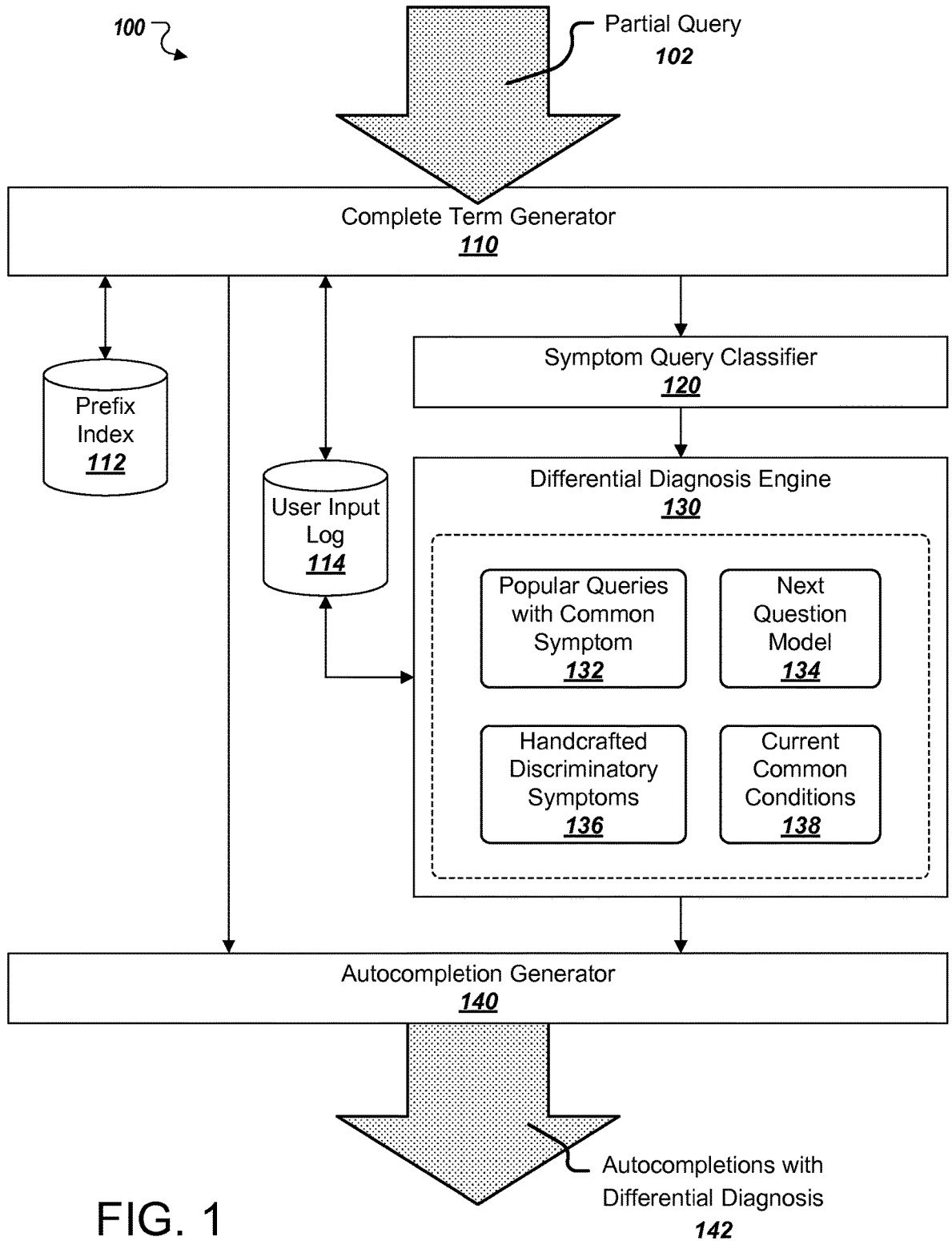
FIG. 1 is a diagram of an exemplary system for generating medically-related search query suggestions using a differential diagnosis approach.

FIG. 1 depicts an exemplary system 100 for generating medically-related search query suggestions using a differential diagnosis approach. The system 100 may, in this example, receive a particular query 102 as an input and, based at least on the partial query 102, provide auto-completions with differential diagnosis 142 as output. The partial query 102 may, for instance, represent input provided by a user to a field of an interface for a search engine. Similarly, the auto-completions with differential diagnosis 142 may represent one or more suggested search queries provided for display on the interface for the search engine. More particularly, the system 100 includes a complete term generator 110, a symptom query classifier 120, a differential diagnosis engine 130, and an auto-completion generator 140. The system 100 may, for example, be implemented on a variety of computing devices.

The complete term generator 110 may generate one or more complete terms based on the partial query 102 that it receives. More specifically, the complete term generator 110 may communicate with a prefix index 112 and a user input log 114 to predict the rest of a term being entered by the user as partial query 102. The prefix index 112 may, for example, include data that associates portions of terms or prefixes to complete terms. The user input log 114 may, for example, include data representative of textual input having been provided in one or more fields of a search engine interface. Such input may, for instance, be provided in one or more fields of a search engine interface by way of one or more text entry interfaces including virtual keyboards, mechanical keyboards, speech recognition systems, voice recognition systems, gesture recognition systems, handwriting recognition systems, or a combination thereof.

The symptom query classifier 120 may receive one or more complete terms generated by the complete term generator 110 and determine whether the partial query 102 is to be considered a symptom query, or has a relatively high likelihood of pertaining to one or more symptoms. Particularly, the symptom query classifier 120 may seek to identify terms that represent symptoms of one or more known medical conditions. The symptom query classifier 120 may, in some examples, reference a list of terms that are associated with medical conditions in order to make such a determination. In some implementations, the symptom query classifier 120 may classify queries using one or more machine learning techniques.

The differential diagnosis engine 130 may receive the one or more terms generated by the complete term generator 110 based on the partial query 102, as well as data output by the symptom query classifier 120 indicating whether the partial query 102 is classified as a symptom query. Additionally, the symptom query classifier 120 may indicate the particular symptom or symptoms that the partial query 102 is associated with.

In response to the symptom query classifier 120 having classified the partial query 102 as a symptom query, the differential diagnosis engine may act to identify one or more differential diagnosis terms used to determine one or more suggested search queries which may prompt user interaction that is telling of particular medical conditions being related or unrelated to the search being conducted and guide users toward information that is pertinent to their specific health issues. The differential diagnosis engine 130 may draw from one or more sets of information that indicate one or more of popular queries with common symptom 132, a next question model 134, handcrafted discriminatory symptoms 136, and current common conditions 138. Such sets of information may, for example, be included in one or more databases accessible to and/or maintained by differential diagnosis engine 130. The differential diagnosis engine 130 may also utilize information in user input log 114 for search query suggestion determinations. Some or all of the information relied upon by the differential diagnosis engine 130 is indicated or incorporated in a knowledge graph. In some implementations, the differential diagnosis engine 130 may further make its determinations on the basis of user information such as information about a user's social network, social actions or activities, profession, a user's preferences, a user's current location, and/or a user's browsing history.

Information associated with popular queries with common symptom 132 may, for instance, serve to indicate search queries that include terminology associated with a particular symptom and the frequency at which each of the search queries are submitted by users of the search engine. The differential diagnosis engine 130 may evaluate information received from the symptom query classifier 120 against popular queries with common symptom 132 to determine one or more search queries that commonly occur with reference to the one or more symptoms represented by partial query 102.

The next question model 134 includes a statistical model that indicates one or more logical steps of a differential diagnosis procedure that may be applied to the one or more symptoms represented by partial query 102. More particularly, the next question model 134 may, for each of multiple medical conditions, indicate a likelihood or confidence score that the given medical condition applies to a search query being entered. The next question model 134 may further indicate one or more values representative of the urgency or severity of each medical condition. With such probabilistic information, the next question model 134 may provide indication of one or more strategies that may be implemented to quickly rule-out critical/serious medical conditions, large number of medical conditions, or a combination thereof.

In this way, the next question model 134 may be seen as indicating what a health care professional's "next question" could be for a patient experiencing such symptoms. Such refinements may be ranked on the basis of statistical data described above so as to enable efficiently and/or accurately refine a list of possible diagnoses by process of elimination. This model may, for example, be developed on the basis of differential diagnosis procedures and medical opinions provided by one or more health care professionals. The next question model 134 may also be referenced by the differential diagnosis engine 130 to rule out various medical conditions and determine which medical conditions remain in contention for diagnosis in real-time as the user forms their search query. In some examples, the next question model 134 may prioritize The handcrafted discriminatory symptoms, as reflected by information set 136, may include symptoms that are specific to one or more medical conditions and whose presence may indicate one or more medical conditions being related or unrelated to the search being conducted. Like the next question model 134, the handcrafted discriminatory symptoms 136 may be determined and modified by a panel of one or more health care professionals.

The current common conditions 138, as reflected by information set 138, may include data indicating one or more conditions that are determined to currently be common. This list of current conditions may, for example, be developed by sourcing data from searches conducted by other users of the search engine, crawling one or more web resources, obtaining data about the specific user, and/or receiving input from one or more health care professionals. In some examples, the list may be developed on the basis of information associated with other users that are social contacts of the specific user, are located in the same geographical region as the specific user, have one or more user profile attributes in common with the specific user, or a combination thereof. The current common conditions 138 may be utilized to adjust the probabilities of conditions, and thus influence the refinements that the differential diagnosis engine 130 seeks to make.

The differential diagnosis engine 130 may refer to the next question model 134 in conjunction with handcrafted discriminatory symptoms 136, current common conditions 138, and other user information in order to determine one or more refinements that are to be made at each step in the differential diagnosis procedure. The differential diagnosis engine 130 may further rely upon popular queries with common symptom 132 in order to map the determined refinements to one or more differential diagnosis terms to include in suggested search queries.

The auto-completion generator 140 may receive input from both the complete term generator 110 and the differential diagnosis engine 130 in order to produce auto-completions with differential diagnosis 142. That is, the auto-completion generator 140 may generate one or more suggested search queries based on the partial query 102, one or more complete terms generated by the complete term generator 110, one or more differential diagnosis terms identified by the differential diagnosis engine 130, and/or one or more additional query revision strategies. In examples in which the symptom query classifier 120 determines that the partial query received is not classified as a symptom query, the auto completion generator 140 may proceed to rely upon input from the complete term generator 110 to produce suggested search queries using one or more other query revision strategies.

The auto-completions with differential diagnosis 142 may include one or more suggested search queries that are provided for user selection on a search engine interface. For example, auto-completions with differential diagnosis 142 may be provided in a drop-down menu below a search box of the search engine interface or within the search box itself. In some implementations, these health-related suggested search queries may appear along with other suggested search queries that are not health-related or in a substantially similar manner as such other suggested search queries. In this way, the user may be unaware that the search engine is performing any sort of differential diagnosis procedure. In other implementations, the user may be provided with data indicating that a differential diagnosis procedure is being performed. In these implementations, the user may ultimately be provided with one or more diagnoses in a form other than suggest search queries. For instance, the search engine interface may indicate a list of one or more probable diagnoses. The auto-completions with differential diagnosis 142 may also be further relied upon by the differential diagnosis engine 130 or other components of system 100 for current and/or future diagnoses. In some implementations, the auto-completions with differential diagnosis 142 and/or other data produced by symptom query classifier 120 and differential diagnosis engine 130 may be relied upon by the search engine to tailor one or more sets of search results provided in response to search queries for health-related information.

Figure 2:
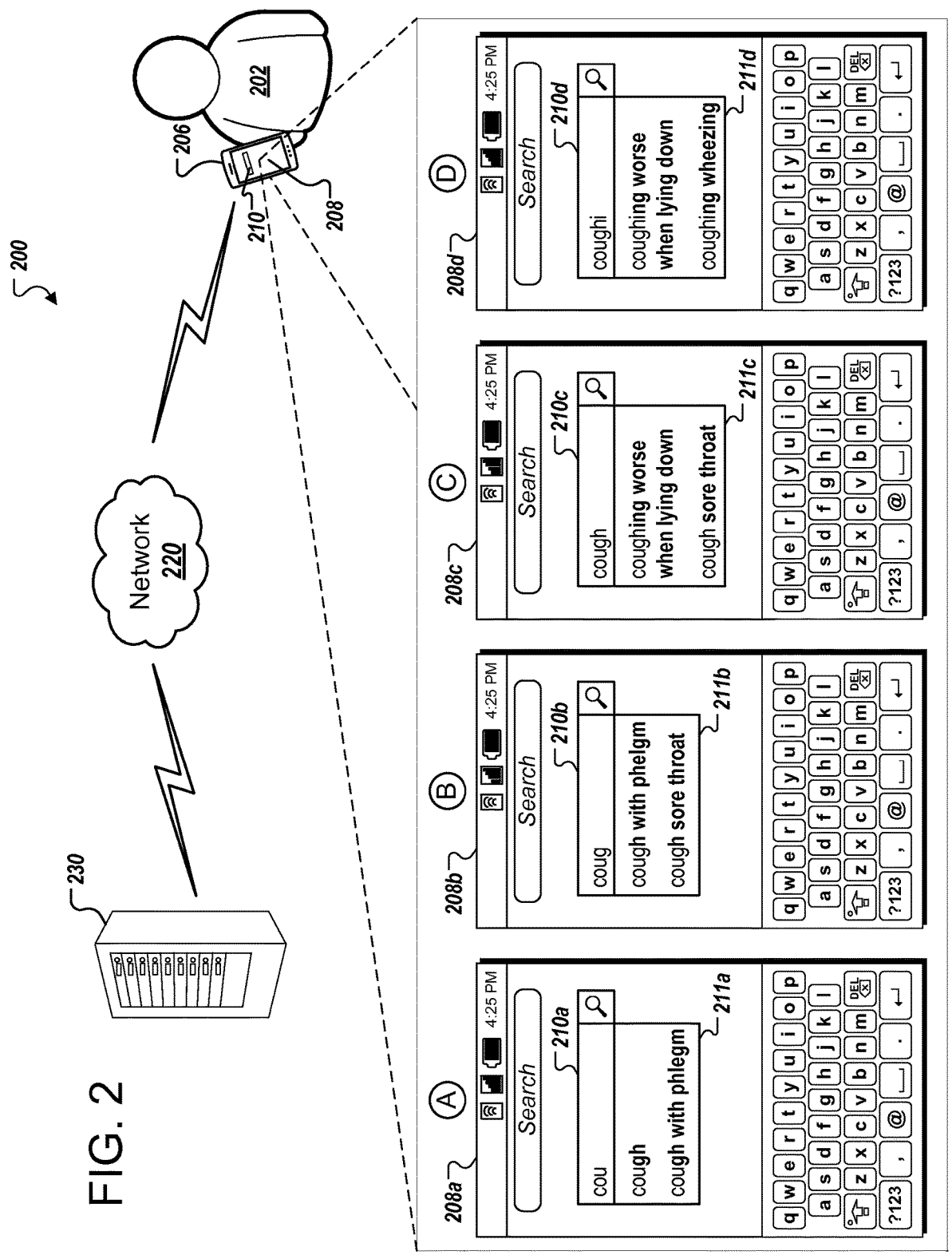
FIG. 2 is a conceptual diagram of an exemplary framework for generating medically-related search query suggestions using a differential diagnosis approach.

FIG. 2 is a conceptual diagram of an exemplary framework for generating medically-related search query suggestions using a differential diagnosis approach in a system 200. The techniques described in reference to system 200 may, for example, be similar to those which have been described above in association with FIG. 1. More particularly, the diagram depicts a client device 206 in communication with a computing device 230 over a network 220, that collectively make up system 200. The diagram also depicts a screen 208 that is displayed by a screen of the client device 206 in various stages, labeled as form 208a to 208d, in time-sequenced stages "A" to "D," respectively. Briefly, and as described in further detail below, the client device 206 may receive input for a search query field and may display one or more suggested search queries.

A user 202 of the client device 206 may initiate a search for information stored on a public or private network by entering a part of a query term, or one or more full or complete query terms into a search box 210 of the user interface 208. The user interface 208 may correspond to an interface provided by a search application that the user 202 has accessed. The computing device 230 may, for example, include or operate in cooperation with a search engine. In general, the client device 206 and the computing device 230 interact using a query and response approach, in that the client device 206 sends a search query request that includes one or more query terms (such as an entered query term) to the computing device 230, and the computing device 230 executes the search query using the query terms and responds with information identifying a set of search results. This information may be formatted as a hypertext markup language (HTML) document that the client device 206 processes in order to display a search engine results page. Using the entered query term, the computing device 230 may execute search queries for information stored on public networks (e.g., the Internet) or private networks (e.g., an intranet server).

In some implementations, the processes described in association with FIG. 1 may be performed at least in part by computing device 230. In these implementations, processes described in association with FIGS. 1 and 2 may also be handled or performed by other cloud computing devices that are communicatively coupled with one or more of client device 206 and computing device 230. In other implementations, the processes described in association with FIG. 2 may be performed in part or entirely by client device 206.

When a user enters a query term into search box 210 or other form of search field, a search engine may respond by generating and providing suggested search queries using a differential diagnosis search query revision strategy similar to that which has been described above in association with FIG. 1. In some examples, the differential diagnosis search query revision strategy of FIG. 1 may be implemented in combination with one or more other appropriate query revision strategies. In one example, a suggested search query may be a full word that the user had just started to type, or a suggested search query that the user had selected in the past. In another example, a suggested search query may be a term that, when it was used by other users of the search engine in the past to execute search queries, generated search results that were more satisfying to those users than a search result that was generated using the query term that the user entered. In other examples, the suggested search query may be a term that the user might have intended to enter, or would have entered had the user either been more experienced with using the search engine, or been aware of additional facts. The suggested search queries of the examples above may be generated and provided based at least on a received partial query received and one or more identified differential diagnosis terms.

In stage A, the client device 206 may display user interface 208a having search box 210a that includes a partial query entered by user 202. In this example, the partial query includes the textual string "cou." Using a system similar to that which has been described above in association with FIG. 1, one or more suggested search queries 211a may be provided based on the partial query entered by user 202. In the example of stage A, the one or more suggested search queries 211a for a partial query of "cou" may include "cough" and "cough with phlegm." The suggested search query of "cough with phlegm" may represent a suggestion for a discriminatory symptom. For instance, there may be a set of medical conditions for which a cough accompanied by phlegm is a symptom. By gauging the user's response to this suggested search query, the search engine may be able to either rule out the set of medical conditions for which a cough accompanied by phlegm is a symptom or a disjoint set of medical conditions. This discriminatory symptom may, for instance, be provided at an early stage of the differential diagnosis process to rule out one or more serious medical conditions and/or a large number of medical conditions.

In stage B, the client device 206 may display user interface 208b having search box 210b that includes a partial query entered by user 202. In this example, the partial query includes the textual string "coug." Using a system similar to that which has been described above in association with FIG. 1, one or more suggested search queries 211b may be provided based on the partial query entered by user 202. In the example of stage B, the one or more suggested search queries 211b for a partial query of "coug" may include "cough with phlegm" and "cough sore throat." The suggested search query of "cough with phlegm" may represent a suggestion for the discriminatory symptom previously provided in stage A. It can be noted that user 202 did not select any of the suggested search queries provided in stage A.

In stage C, the client device 206 may display user interface 208c having search box 210c that includes a partial query entered by user 202. In this example, the partial query includes the textual string "cough." Using a system similar to that which has been described above in association with FIG. 1, one or more suggested search queries 211c may be provided based on the partial query entered by user 202. In the example of stage C, the one or more suggested search queries 211c for a partial query of "cough" may include "coughing at night" and "cough sore throat." Since the system 200 provided "cough with phlegm" as a suggested search query in stages A and B and it was not subsequently selected by the user 202, the system 200 may refrain from providing it as a suggested search query, once again, in stage C. Furthermore, the system 200 may interpret the user 202 neglecting this particular suggested search query as an indication of the set medical conditions for which a cough accompanied by phlegm is a symptom being unlikely diagnoses. That is, the system 100 may rule out medical conditions for which "cough with phlegm" is a symptom based on the user 202 failure to select its corresponding suggested search query or other indicate intent to submit a search query of this nature. Upon ruling out this set of medical conditions, the system 200 may have determined to suggest "coughing at night" and continue to suggest "cough sore throat" in an effort to further refine its list of possible diagnoses and/or guide the user 202 toward formulating an effective search query for health-related information.

Consider an example in which the system 200 has, in stage C, concluded that the three most likely medical conditions include asthma, gastroesophageal reflux disease (GERD), and congestive heart failure. It can be noted that these medical conditions are often associated with a dry cough that isn't accompanied by phlegm. The cough associated with congestive heart failure, which may be considered the most serious remaining medical condition, is known to worsen when lying down.

Furthermore, the cough associated with asthma or GERD is less likely to be positional. For at least these reasons, the system 200 may consider indication of the position in which a cough worsens or subsides to be a discriminatory factor between congestive heart failure, GERD and asthma. That is, the system 200 can determine that two of these three conditions are less likely simply by determining that the cough worsens on lying down. In the example of stage C, the system 200 may provide the suggested search query of "coughing worse when lying down" in order to further refine the list of possible diagnoses.

In stage D, the client device 206 may display user interface 208*d* having search box 210*d* that includes a partial query entered by user 202. In this example, the partial query includes the textual string "coughi." Using a system similar to that which has been described above in association with FIG. 1, one or more suggested search queries 211*d* may be provided based on the partial query entered by user 202. In the example of stage D, the one or more suggested search queries 211*d* for a partial query of "coughi" may include "coughing worse when lying down" and "coughing wheezing." It can be noted that the system 200 continues to provide the suggested search query of "coughing at night," but refrains from displaying "cough sore throat" again. Although the user 202 has yet to select a suggested search query, the system 200 may interpret the user 202 having modified the partial search query from "cough" in stage C to "coughi" in stage D as an indication that the user 202 may be favoring the "coughing at night" suggested search query. At the least, system 200 may provide suggested search queries that include the term "coughing" based on the complete query generator receiving a partial query of "coughi." Following the example described above, the system 200 may provide the partial query of "coughing wheezing" in stage D, which is a known symptom of asthma. By presenting suggested search queries 211*d*, the system 200 may, in this example, be able to suggest possible diagnoses with a relatively high level of confidence following the actions of user 202 that follow stage D.

Figure 3:
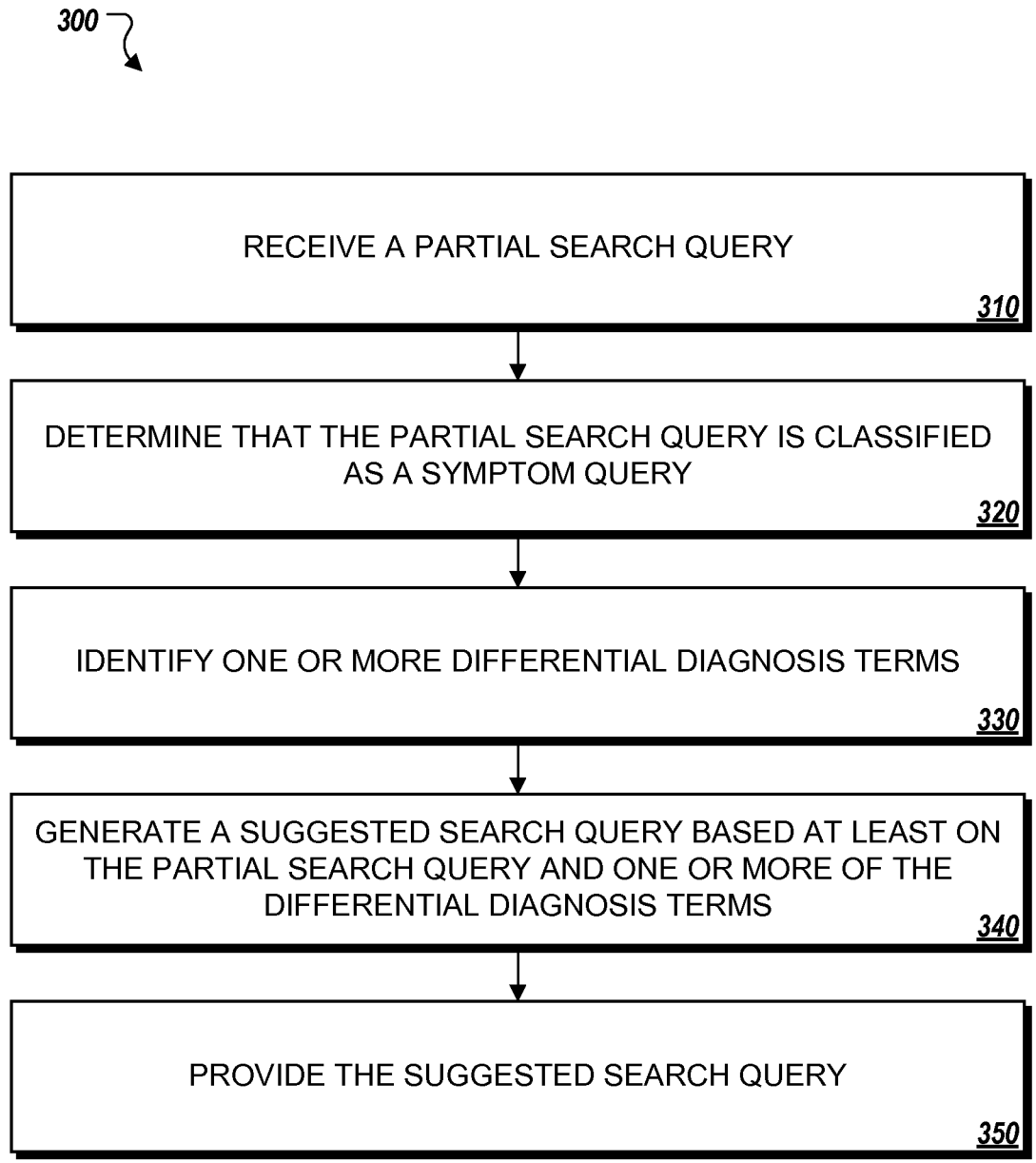
FIG. 3 is a flowchart of an example process for generating medically-related search query suggestions using a differential diagnosis approach.

FIG. 3 illustrates exemplary process 300 for generating medically-related search query suggestions using a differential diagnosis approach. The following describes the process 300 as being performed by components of systems that are described with reference to FIGS. 1-2. However, the process 300 may be performed by other systems or system configurations. Briefly, the process 300 may include receiving a partial search query (310), determining that the partial search query is classified as a symptom query (320), identifying one or more differential diagnosis terms (330), generating a suggested search query based at least on the partial search query and one or more of the identified terms (340), and providing the suggested search query (350).

In more detail, the process 300 may include receiving a partial query (310). For example, this may correspond to the complete term generator 110 receiving partial query 102. The process 300 may include determining that the partial search query is classified as a symptom query (320). This may, for instance, correspond to symptom query 120 determining that the partial query 102 is classified as a symptom query based on the input it receives from the complete term generator 110.

The process 300 may include identifying one or more differential diagnosis terms (330). For example, this may correspond to the differential diagnosis engine 130 identifying one or more differential diagnosis terms based on input received from symptom query classifier 120, user input log 114, popular queries with common symptom 132, next question model 134, handcrafted discriminatory symptoms 136, current common conditions, user information, or a combination thereof.

The process 300 may further include generating a suggested search query based at least on the partial search query and one or more of the differential diagnosis terms (340). As described above, this may correspond to the auto-completion generator 140 developing one or more suggested search queries based on input received from the complete term generator 110 and differential diagnosis engine 130. The process 300 may include providing the suggested search query in response to the partial search query (350). For instance, this may correspond to the system 100 providing the auto-completions with differential diagnosis 142 in response to partial query 102. Such auto-completions may, for example, be provided to one or more output devices including visual displays, haptic displays, text-to-speech systems, or a combination thereof. The actions described in association with process 300 may, for example, be performed continuously as a search query is being entered by a user.

Figure 4:
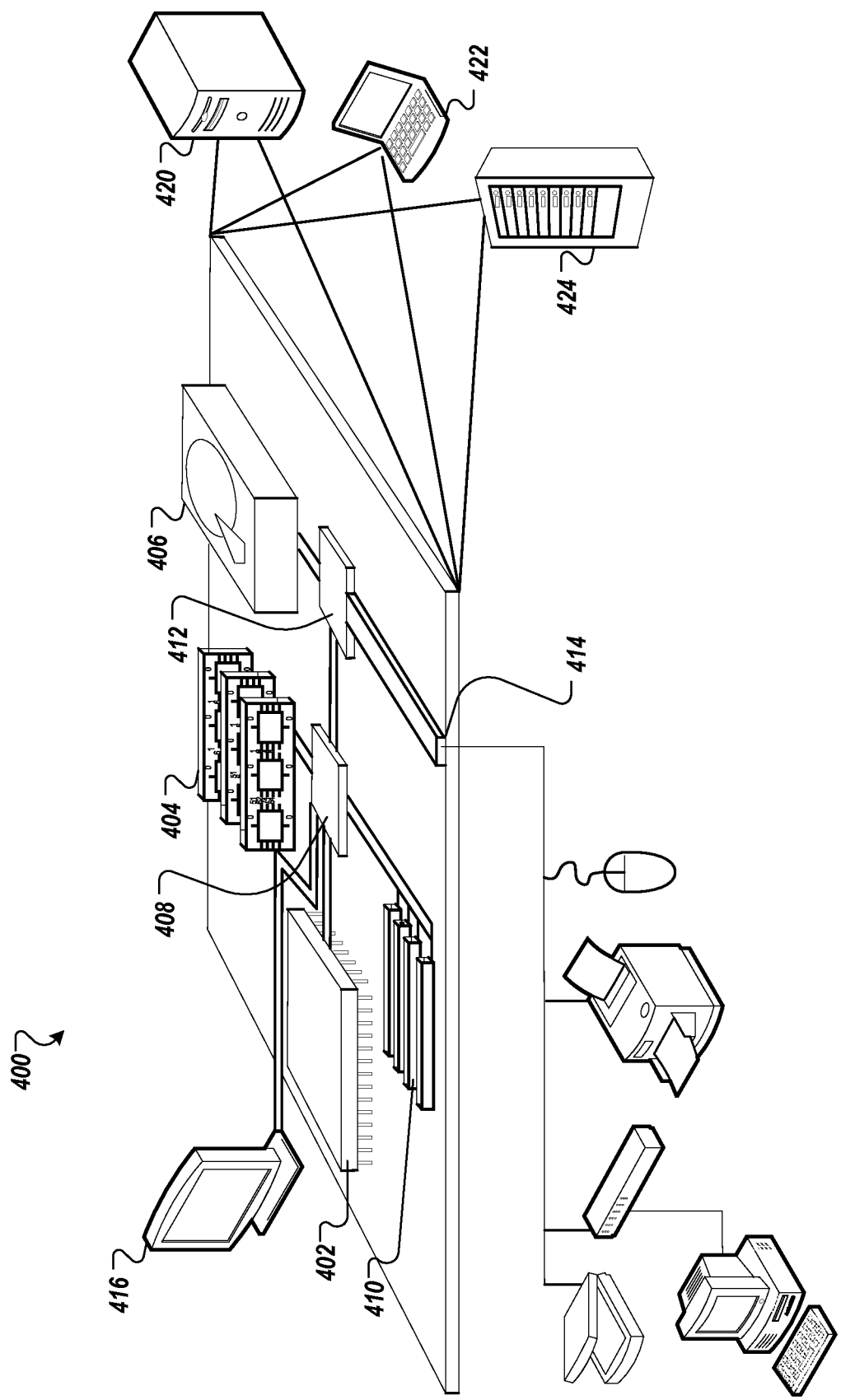
FIG. 4 is a diagram of exemplary computing devices.

FIG. 4 is a block diagram of computing devices 400 that may be used to implement the systems and methods described in this document, as either a client or as a server or plurality of servers. Computing device 400 is intended to represent various forms of digital computers, such as laptops, desktops, workstations, personal digital assistants, servers, blade servers, mainframes, and other appropriate computers.

Computing device 400 includes a processor 402, memory 404, a storage device 406, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations, e.g., as a server bank, a group of blade servers, or a multi-processor system.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown). Each of such devices may contain one or more of computing device 400 and an entire system may be made up of multiple computing devices 400 communicating with each other.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method comprising:
receiving, by a search engine system that includes (i) a complete term generator, (ii) a symptom query classifier, (iii) a differential diagnosis engine, and (iv) an auto-completion generator, a partial search query that includes an incomplete query term;
generating, by the complete term generator of the search engine system, a complete query term that is associated with the incomplete query term received by the search engine system;
determining, by the symptom query classifier of the search engine system and based at least on the complete query term that is associated with the incomplete query term received by the search engine system, that the partial search query is classified as a symptom query;
in response to determining that the partial search query is classified as a symptom query, identifying, by the differential diagnosis engine of the search engine system, one or more differential diagnosis terms for refining a set of possible diagnoses that are associated with one or more symptoms indicated by the complete query term;
generating, by the auto-completion generator of the search engine system, a first suggested search query based at least on (i) the partial search query, and (ii) one or more of the differential diagnosis terms;
providing, by the search engine system, the first suggested search query in response to the partial search query, the first suggested search query being an auto-completion of the incomplete query term of the partial search query;
receiving, by the search engine system, additional input for the incomplete query term, wherein the additional input matches at a portion of the first suggested search query, and wherein the additional input is not a selection of the first suggested search query;
in response to receiving the additional input for the incomplete query term and the first suggested search query not being selected:
identifying one or more medical conditions associated with the partial search query and the additional input, wherein the one or more medical conditions do not include medical conditions that have, as a symptom of the medical condition, the first suggested search query in response to the first suggested search query not being selected; and
generating, by the auto-completion generator of the search engine system, a second suggested search query based at least on (i) the partial search query with the additional input, (ii) one or more of the differential diagnosis terms, and (iii) the one or more medical conditions.

2. The computer-implemented method of claim 1, wherein identifying one or more differential diagnosis terms comprises identifying one or more terms that are associated with the one or more medical conditions.

3. The computer-implemented method of claim 2, further comprising:
accessing, for each of the one or more medical conditions, a handcrafted differential diagnosis database for the medical condition; and
wherein identifying one or more differential diagnosis terms that are associated the one or more medical conditions comprises identifying one or more terms that are associated with a symptom of each of the one or more medical conditions based on the handcrafted differential diagnosis database for the medical condition.

4. The computer-implemented method of claim 1, wherein determining that the partial search query is classified as a symptom query comprises classifying the partial search query against multiple symptom query classifiers that are each associated with different medical conditions.

5. The computer-implemented method of claim 1, wherein identifying one or more differential diagnosis terms comprises identifying one or more differential diagnosis terms based on one or more recent popular queries.

6. The computer-implemented method of claim 1, wherein identifying one or more differential diagnosis terms comprises identifying one or more differential diagnosis terms based on a statistical model.

7. The computer-implemented method of claim 1, wherein determining that the partial search query is classified as a symptom query comprises:
determining that the partial search query is classified as a search query that includes at least a portion of a term corresponding to one or more medical conditions.

8. A search engine system including (i) a complete term generator, (ii) a symptom query classifier, (iii) a differential diagnosis engine, and (iv) an auto-completion generator, the search engine system comprising:
one or more computers; and
a non-transitory computer-readable medium coupled to the one or more computers having instructions stored thereon, which, when executed by the one or more computers, cause the one or more computers to perform operations comprising:
receiving a partial search query that includes an incomplete query term;
generating, by the complete term generator, a complete query term that is associated with the incomplete query term received by the search engine system;
determining, by the symptom query classifier and based at least on the complete query term that is associated with the incomplete query term received by the search engine system, that the partial search query is classified as a symptom query;
in response to determining that the partial search query is classified as a symptom query, identifying, by the differential diagnosis engine, one or more differential diagnosis terms for refining a set of possible diagnoses that are associated with one or more symptoms indicated by the complete query term;

generating, by the auto-completion generator of the search engine system, a first suggested search query based at least on (i) the partial search query, and (ii) one or more of the differential diagnosis terms;

providing, by the search engine system the first suggested search query in response to the partial search query, the first suggested search query being an auto-completion of the incomplete query term of the partial search query;

receiving, by the search engine system, additional input for the incomplete query term, wherein the additional input matches at a portion of the first suggested search query, and wherein the additional input is not a selection of the first suggested search query; and in response to receiving the additional input for the incomplete query term and the first suggested search query not being selected:

identifying one or more medical conditions associated with the partial search query and the additional input, wherein the one or more medical conditions do not include medical conditions that have, as a symptom of the medical condition, the first suggested search query in response to the first suggested search query not being selected; and generating, by the auto-completion generator of the search engine system, a second suggested search query based at least on (i) the partial search query with the additional input; (ii) one or more of the differential diagnosis terms, and (iii) the one or more medical conditions.

9. The search engine system of claim 8, wherein identifying one or more differential diagnosis terms comprises identifying one or more terms that are associated with the one or more medical conditions.

10. The search engine system of claim 9, wherein the operations comprise:

accessing, for each of the one or more medical conditions, a handcrafted differential diagnosis database for the medical condition; and wherein identifying one or more differential diagnosis terms that are associated the one or more medical conditions comprises identifying one or more terms that are associated with a symptom of each of the one or more medical conditions based on the handcrafted differential diagnosis database for the medical condition.

11. The search engine system of claim 8, wherein determining that the partial search query is classified as a symptom query comprises classifying the partial search query against multiple symptom query classifiers that are each associated with different medical conditions.

12. The search engine system of claim 8, wherein identifying one or more differential diagnosis terms comprises identifying one or more differential diagnosis terms based on one or more recent popular queries.

13. The search engine system of claim 8, wherein identifying one or more differential diagnosis terms comprises identifying one or more differential diagnosis terms based on a statistical model.

14. The search engine system of claim 8, wherein determining that the partial search query is classified as a symptom query comprises:

determining that the partial search query is classified as a search query that includes at least a portion of a term corresponding to one or more medical conditions.

* * * * *

UNITED STATES PATENT AND TRADEMARK OFFICE
CERTIFICATE OF CORRECTION

| | |
|---|---|
| PATENT NO. | : 10,929,413 B2 |
| APPLICATION NO. | : 14/940304 |
| DATED | : February 23, 2021 |
| INVENTOR(S) | : Ramaswami et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 686 days.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*